US 6,568,244 B2

(12) United States Patent
Binz et al.

(10) Patent No.: US 6,568,244 B2
(45) Date of Patent: May 27, 2003

(54) MEASURING AND EVALUATING DEVICE

(75) Inventors: Dieter Binz, Hirschberg (DE); Olaf Krusemark, Hamburg (DE); Uwe Lehmann, Hamburg (DE); Jörg Müller, Buchholz (DE); Albrecht Vogel, Stutensee (DE); Sean Keeping, West Croydon (GB)

(73) Assignee: ABB Research Ltd., Zurich (CH)

( * ) Notice: Subject to any disclaimer, the term of this patent is extended or adjusted under 35 U.S.C. 154(b) by 0 days.

(21) Appl. No.: 09/813,268

(22) Filed: Mar. 20, 2001

(65) Prior Publication Data
US 2001/0029772 A1 Oct. 18, 2001

(30) Foreign Application Priority Data
Mar. 20, 2000 (DE) .......................... 100 13 561

(51) Int. Cl.[7] .................. G01N 19/10; G01N 30/02; B01D 53/02; B01D 15/08
(52) U.S. Cl. .................. 73/23.2; 96/101; 210/198.2; 436/161
(58) Field of Search .............. 73/23.2, 23.35, 73/23.37, 23.4, 23.42; 96/102, 101, 106; 210/198.2; 436/161

(56) References Cited

U.S. PATENT DOCUMENTS

| | | | | |
|---|---|---|---|---|
| 3,630,006 A | * | 12/1971 | Sandoval ................. 96/101 |
| 3,678,656 A | * | 7/1972 | Brunnee et al. ........... 96/106 |
| 4,471,647 A | * | 9/1984 | Jerman et al. ............ 73/23.4 |
| 4,474,889 A | * | 10/1984 | Terry et al. ............. 436/161 |
| 4,888,295 A | * | 12/1989 | Zaromb et al. .......... 436/161 |
| 4,891,120 A | * | 1/1990 | Sethi et al. ............. 204/600 |
| 5,116,495 A | * | 5/1992 | Prohaska .............. 210/198.2 |
| 5,132,012 A | * | 7/1992 | Miura et al. .......... 210/198.2 |
| 5,514,832 A | * | 5/1996 | Dusablon, Sr. et al. ... 174/15.1 |
| 5,525,799 A | * | 6/1996 | Andresen et al. .......... 250/288 |
| 5,611,846 A | * | 3/1997 | Overton et al. ............ 96/102 |
| 5,983,703 A | * | 11/1999 | Wylie et al. ............ 73/23.42 |
| 6,068,780 A | * | 5/2000 | Yu ......................... 216/10 |
| 6,096,656 A | * | 8/2000 | Matzke et al. ............ 438/702 |
| 6,351,983 B1 | * | 3/2002 | Haas et al. ............. 73/23.37 |
| 6,354,136 B1 | * | 3/2002 | Bremer et al. .......... 73/23.35 |

FOREIGN PATENT DOCUMENTS

DE      3729775      * 9/1987 .......... G01N/30/60

* cited by examiner

Primary Examiner—Hezron Williams
Assistant Examiner—Jay L. Politzer
(74) Attorney, Agent, or Firm—Laurence A. Greenberg; Werner H. Stemer; Ralph E. Locher

(57) ABSTRACT

A measuring and evaluating device for the analysis of gases is described. The device has an exchangeable gas analyzer, which is of small dimensions. The gas analyzer is a module connected directly from the outside to a central unit, which is likewise of small dimensions and into which at least one evaluating unit and a display unit are integrated. Fitted releasably into the gas analyzer are one or more plates, into which at least one separating channel is respectively integrated. Each gas analyzer is provided with at least one sample injector, which can be connected to at least one separating channel. At least one detector is connected downstream of each separating channel.

5 Claims, 10 Drawing Sheets

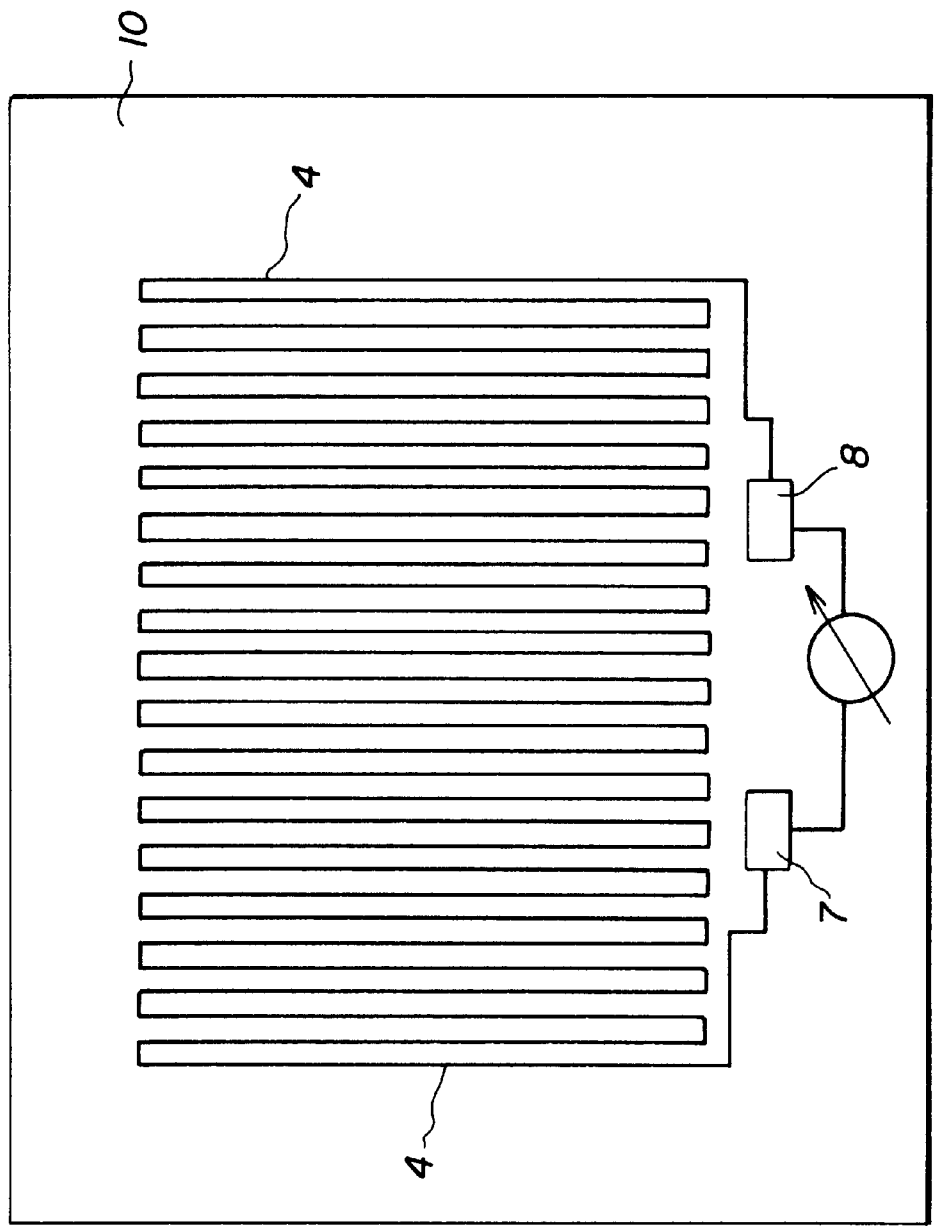

MEASURING AND EVALUATING DEVICE

BACKGROUND OF THE INVENTION

Field of the Invention

The invention relates to a measuring and evaluating device.

Such devices are used where the composition of gases has to be known for the control and/or regulation of a process. For determining the composition of gas, gas analyzers are used. The measured values determined by these devices are passed to an evaluating device separate from them. In the case of these devices, the accuracy of an analysis essentially depends on the use of suitable separating materials, detectors, the carrier gas and the operating conditions. The analysis time is essentially determined by the length of the separating column and the flow rate of the carrier gas/sample gas mixture through the separating column. The separating column used must in this case be all the longer the more similar the separating behavior of the components in the gas sample and the faster the travel rate of the gas sample through the separating column. For example, separating columns of 50 m in length are nowadays required for the separation of methane and ethane in the analysis of natural gas. For the analysis of high-boiling, long-chain hydrocarbons in the form of C5–C12, a length of 3 to 10 m is sufficient. Here it is also disadvantageous that with these devices the analysis times are very long. In the case of gas analyses for online process control, however, a short analysis time is very important. Furthermore, the application conditions in process gas analysis are such that the approximate composition of the medium to be investigated is known, and the intention is to determine the exact volume fraction of the main gas constituents. In the known process gas chromatographs, a short analysis time is achieved by using not just one separating column but generally at least two. In this case, a high-speed preliminary separation of the gas sample is carried out in a first column, with the fractions of the gas sample that are not of interest being separated out. Then, only those constituents of which the fractions are to be exactly determined are passed into the separating column. The production of such process gas chromatographs is very complex and expensive. The separating columns, valves and detectors have to be made individually for each device and put together individually for the respective application. Further essential, high-cost components of such a process gas chromatograph are the column oven and the housing. The column oven is required to allow the separating column to be operated at an increased, constant temperature of, for example, 70° C. An increased temperature speeds up the transport of low-volatility components in the sample. Also known are special methods in which the sample is vaporized abruptly. With flash vaporizing, the readily volatile constituents are quickly separated out. For this purpose, the temperature of the column oven must be changed from, for example, 40° C. to 140° C. within just a few seconds. Another likewise known type of application of the column oven is operation with a slow temperature ramp, for example in the range between 40° C. and 150° C.

SUMMARY OF THE INVENTION

It is accordingly an object of the invention to provide a measuring and evaluating device that overcomes the above-mentioned disadvantages of the prior art devices of this general type, which has small dimensions with which process gas analyses can be carried out simply and quickly and the measurement results can be evaluated and displayed immediately.

With the foregoing and other objects in view there is provided, in accordance with the invention, a measuring and evaluating device for performing an analysis of gases. The device contains a central unit, at least one gas analyzer removably connected to the central unit, at least one evaluating unit integrated in the central unit, and a display unit integrated in the central unit and connected to the evaluating unit.

The measuring and evaluating device according to the invention is equipped with the gas analyzer configured as a module. This is releasably connected to the central unit of the measuring and evaluating device. The length and height of the central unit are less than 25 cm. Its width is less than 10 cm. The size of the gas analyzer is matched to these dimensions. Consequently, the measuring and evaluating unit can be easily transported and used at different locations. The central unit is provided, inter alia, with an evaluating unit, a display device and a power supply unit. Integrated in the gas analyzer are the components required for investigating a gas, such as a sample injector, a separating channel and detectors in the configuration required for taking samples, forward flushing, back flushing and also heart-cut or flip-flop operation.

In accordance with an added feature of the invention, the gas analyzer is a module and is connected directly to the central unit from the outside and is also connected to the evaluating unit. A power supply unit for supplying electrical power is integrated in the central unit. The central unit has supply lines ending in a plug-in connection for transporting a carrier gas, a gas to be analyzed and a calibrating gas, respectively.

In accordance with an additional feature of the invention, the gas analyzer has at least one plate and at least one separating channel integrated in the plate and the separating channel is releasably fitted in the gas analyzer.

In accordance with another feature of the invention, the plate has recesses formed therein functioning as the separating channel. A cover closes off the separating channel, and a separating material is applied to inside surfaces of the recesses and to inside surface of the covering facing the recesses, at least in a region of the separating channel.

In accordance with a further feature of the invention, the separating channel has a U-shaped cross section, and the plate and the covering are formed from a material selected from the group consisting of silicon, glass, metal and plastic. In addition, the separating material is hexamethyl disiloxane.

In accordance with a further added feature of the invention, the gas analyzer has at least one sample injector connected to the separating channel, and at least one detector is connected downstream of the separating channel.

In accordance with a further additional feature of the invention, the gas analyzer has a further detector connected upstream of the separating channel.

In accordance with another added feature of the invention, the separating channel is one of at least two separating channels provided in the gas analyzer. The sample injector is connected from the evaluating unit to at least one of the separating channels, and the separating channels are connected to the detector.

In accordance with another additional feature of the invention, the gas analyzer has at least one line for connecting the sample injector, the separating channel, and the detector to one another.

In accordance with an embodiment of the invention, the sample injector has at least three supply lines for transporting the carrier gas, the gas to be investigated and the calibrating gas, and are connected to the plug-in connection of a respective one of the supply lines of the central unit.

In accordance with a further embodiment of the invention, at least one heating and cooling device is integrated into either the gas analyzer or the central unit. The heating and cooling device can be a Peltier element. In addition, the heating and cooling device can be formed of a resistance heater and a Peltier element.

Other features which are considered as characteristic for the invention are set forth in the appended claims.

Although the invention is illustrated and described herein as embodied in a measuring and evaluating device, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE DRAWINGS

FIG. 10 is an illustration of the separating channel which is connected in series with two detectors.

DESCRIPTION OF THE PREFERRED EMBODIMENTS

Figure 1:
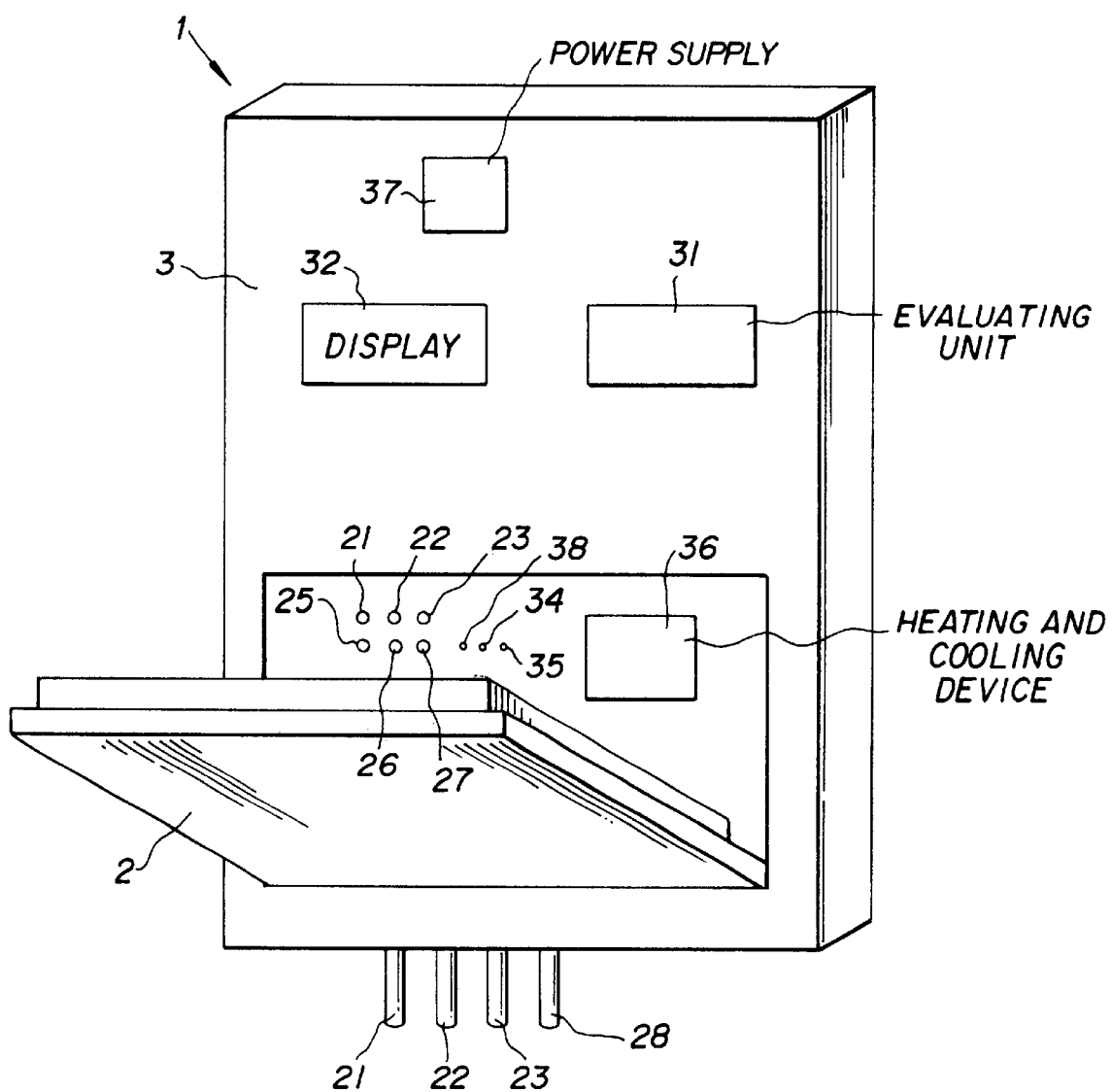
FIG. 1 is a perspective view of a measuring and evaluating device according to the invention.
Figure 2:
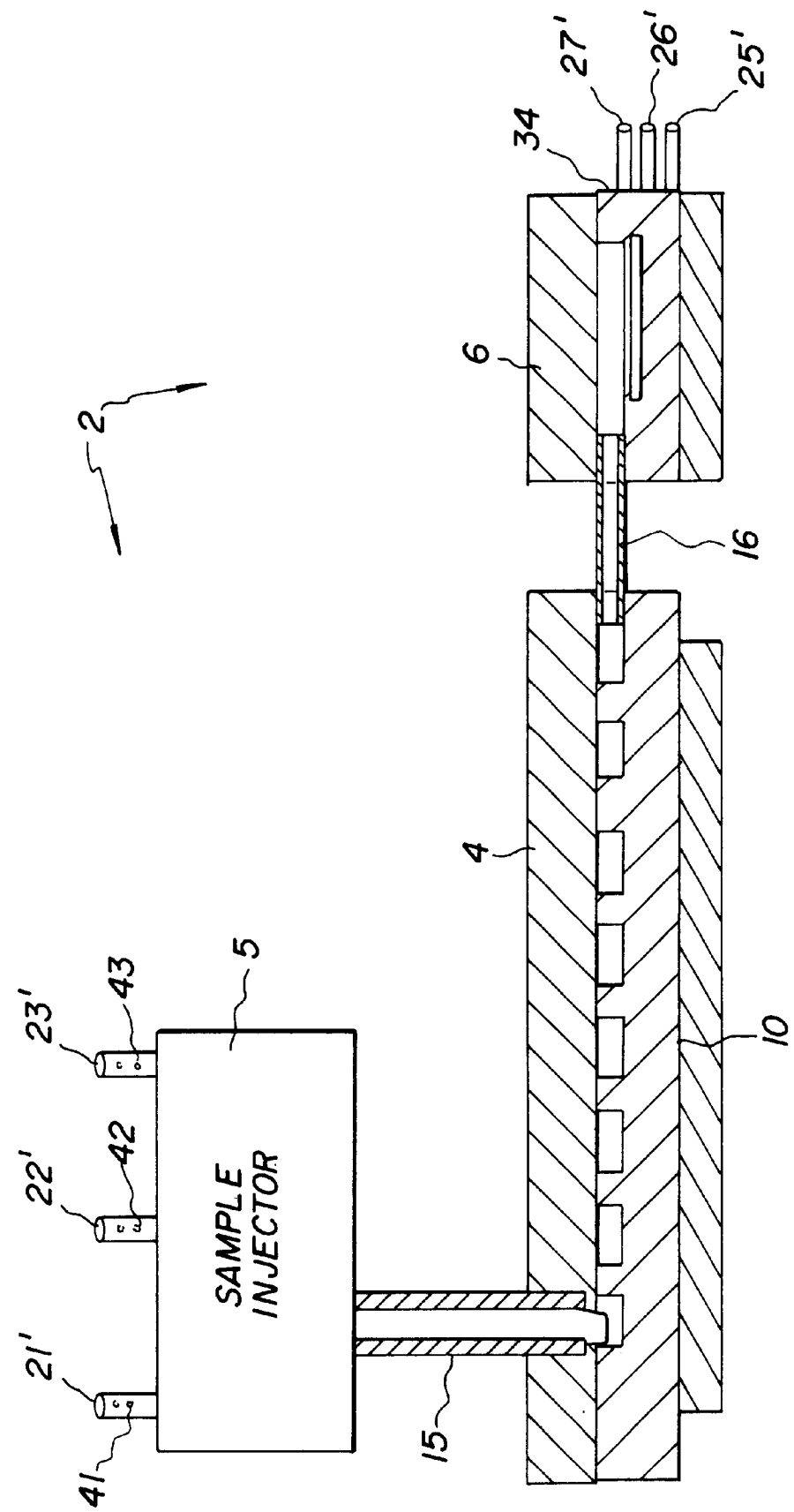
FIG. 2 is an illustration of a gas analyzer.
Figure 3:
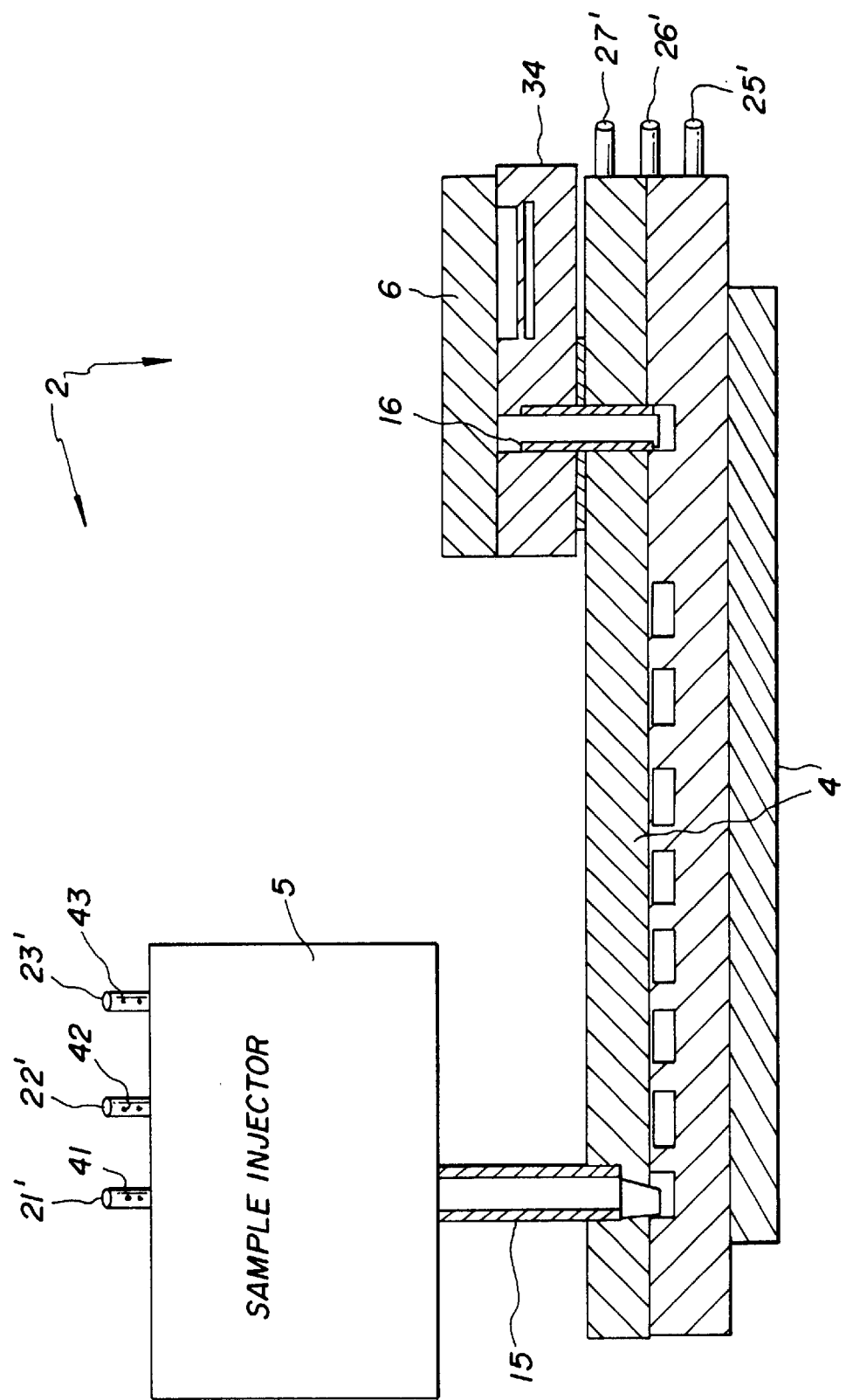
FIG. 3 is an illustration of a variant of the gas analyzer shown in FIG. 2.
Figure 4:
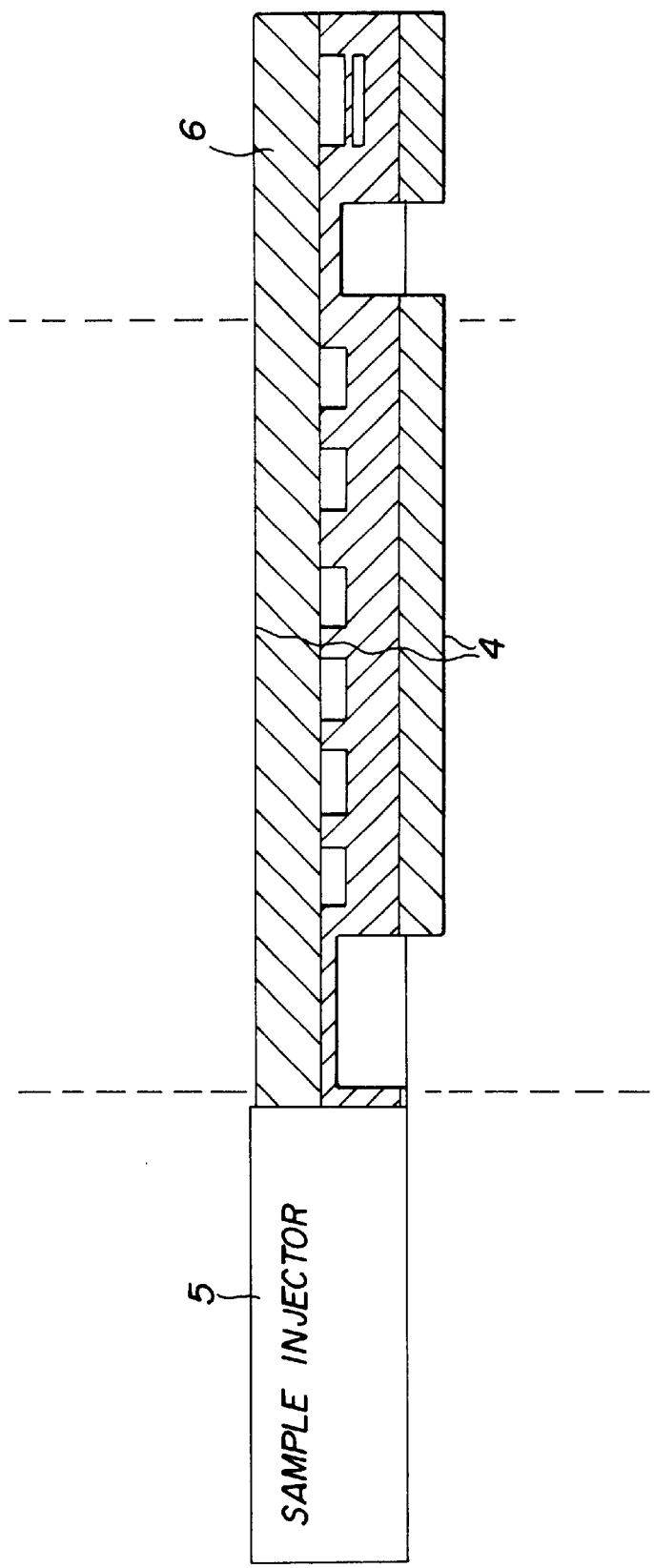
FIG. 4 is an illustration of a further embodiment of the gas analyzer shown in FIG. 3.

In all the figures of the drawing, sub-features and integral parts that correspond to one another bear the same reference symbol in each case. Referring now to the figures of the drawing in detail and first, particularly, to FIG. 1 thereof, there is shown a measuring and evaluating device 1 which contains a gas analyzer 2 and a central unit 3. The gas analyzer 2 is configured as a module. It can be connected electrically and mechanically to the central unit 3 from outside via a releasable connection and can be fastened on the central unit 3. The main construction of the gas analyzer 2 is represented in FIG. 2. In the exemplary embodiment represented here, the gas analyzer 2 is provided with a separating channel 4, a sample injector 5 and a detector 6. As FIGS. 2, 3 and 4 reveal, the sample injector 5, the separating channel 4 and the detector 6 are connected to one another in series. In the exemplary embodiment according to FIG. 2, the sample injector 5 is disposed at a defined distance above the separating channel 4, while the detector 6 is disposed in the same plane as but also at a defined distance from the separating channel 4. This construction is chosen in order to exclude any effects on the measurements of different temperatures occurring within the gas analyzer 2. As FIG. 3 shows, the gas analyzer 2 may also be configured such that the sample injector 5 is installed at a distance above the separating channel 4, while the detector 6 is disposed directly on the surface of the separating channel 4. However, if no significant temperature differences occur within the gas analyzer 2, the gas analyzer 2 may also be configured in such a way that the sample injector 5, the separating channel 4 and the detector 6 are disposed in the same plane directly next to one another (FIG. 4). In all the exemplary embodiments, the separating channel 4 is integrated into a plate 10. In the exemplary embodiment represented here, the plate 10 is produced from silicon. It has a thickness of 500 $\mu$m and a surface area of approximately 10 cm$^2$. The plate 10 may, however, also have other dimensions. Moreover, it may also be produced from a different material in the form of glass, ceramic, metal or plastic.

Figure 5:
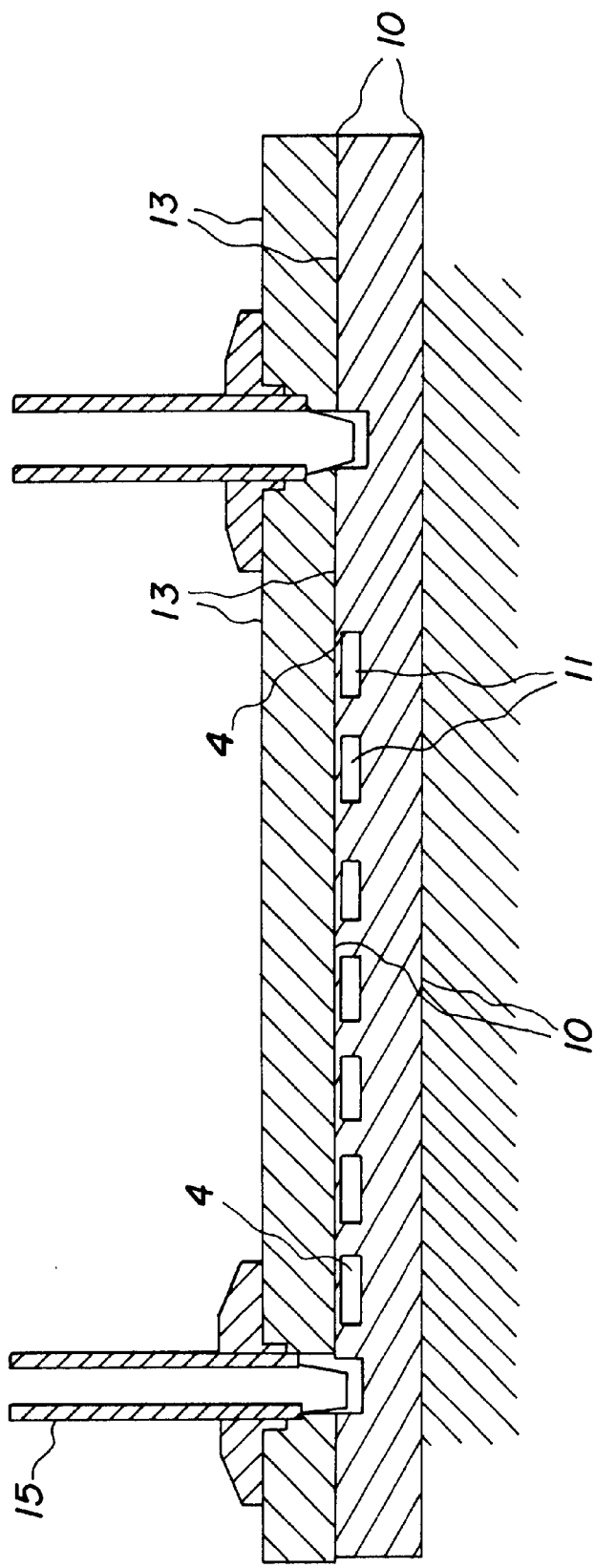
FIG. 5 is an illustration showing the construction of a separating channel.
Figure 6:
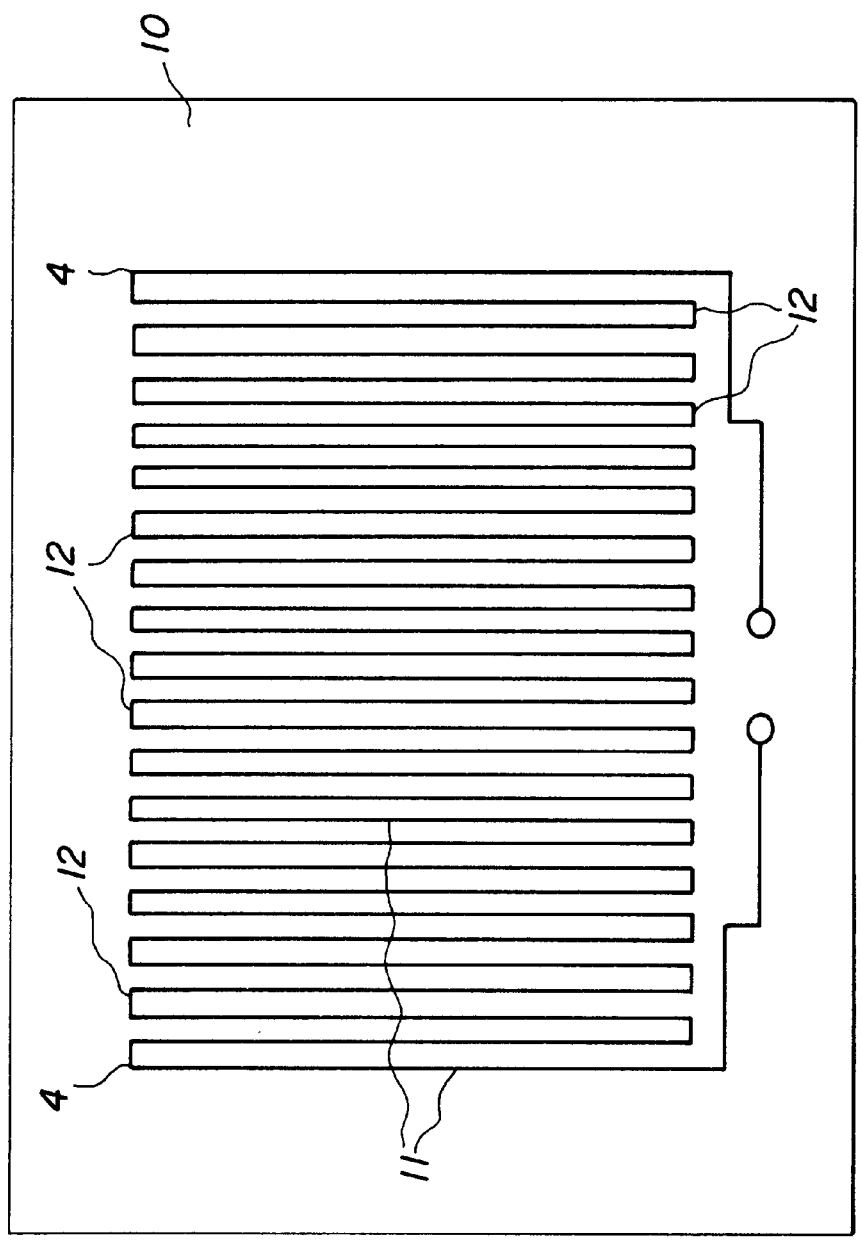
FIG. 6 is a plan view of the separating channel represented in FIG. 5.

In the exemplary embodiment represented in FIG. 4, the sample injector 5 and the detector 6 are also integrated into such a plate 10. The plate 10 is then provided with recesses (not represented here) for receiving the sample injector 5 and the detector 6. As FIG. 5 shows, the plate 10 is provided with U-shaped recesses 11 and 12 for forming the separating channel 4. As can be seen from FIG. 6, pairs of neighboring recesses 11 are disposed parallel to each other at a prescribed distance and are joined to each other in each case at one end via a U-shaped recess 12 in such a way that a continuous, meandering separating channel 4 is formed. The recesses 11, 12 may also be disposed in such a way that a spiral separating channel 4 is formed. The shape of the separating channel 4 respectively used is not restricted to these two embodiments. The recesses 11, 12 are, for example, etched into the surface of the plate 10. However, they may also be formed using a different process. In the exemplary embodiment represented here, the U-shaped recesses 11 and 12 are closed off from the outside by a covering 13 made of glass (FIG. 5). Here, the covering 13 has a thickness of 500 $\mu$m. However, if need be it may also be made thicker or thinner. Instead of glass, the covering 13 may also be made from a different material in the form of ceramic, metal, plastic or silicon.

Figure 7:
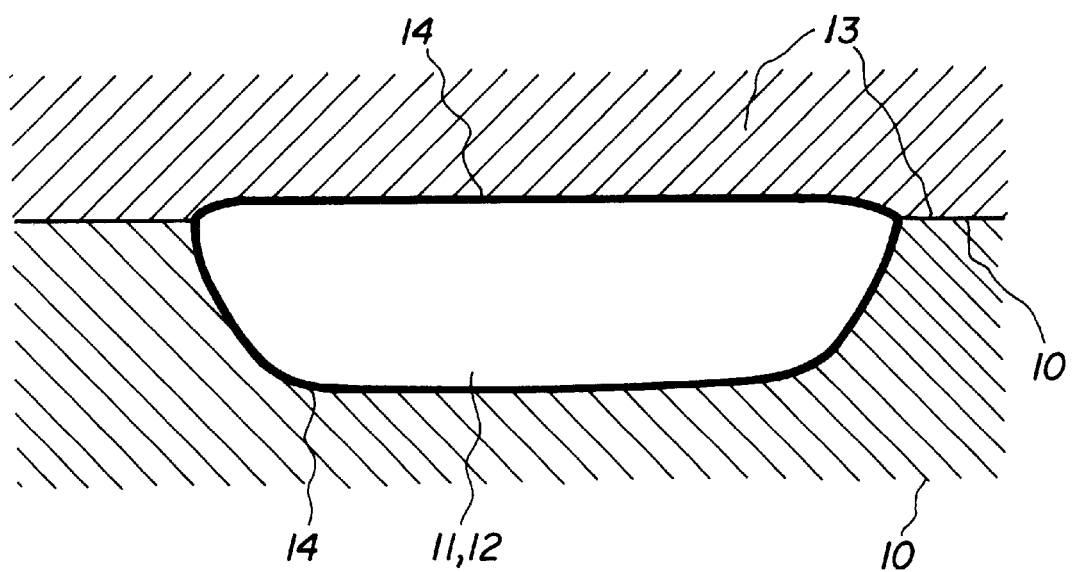
FIG. 7 is an enlarged, sectional view of the separating channel shown in FIG. 6.

FIG. 7 shows an enlarged detail of the separating channel 4 in the region of the recess 11, 12. As FIG. 7 reveals, a separating material 14 has been applied to the inside surface of the recess 11, 12. A metal-organic compound in the form of hexamethyl disiloxane is preferably used for this. The same separating material 14 has been applied to the inside surface of the covering 13, which closes off the recess 11, 12 from the outside. As FIGS. 2, 3 and 5 show, each separating channel 4 is provided with a supply line 15, via which a carrier gas, a gas to be investigated or a calibrating gas (not represented here) can be fed. As FIGS. 2 and 3 show, the separating channel 4 is connected via the supply line 15 to the sample injector 5. In the exemplary embodiment represented in FIG. 4 and explained in the associated description, the line 15 between the sample injector 5 and the separating channel 4 may be formed by a recess (not represented here) in the plate 10 and may be closed off from the outside by the covering 13. A line 16 between the separating channel 4 and the detector 6 may be formed in the same way. The line 16 is used inter alia for the components of the gas to be investigated (not represented here) to reach the detector 6, as represented in FIGS. 2 and 3. A carrier gas 41 fed to the sample injector 5 and a calibrating gas 43 are likewise fed via line 15 to the separating channel 4 and from there via line 16 to the detector 6. Since the gas analyzer 2 is fastened releasably on the central unit 3, a different gas analyzer 2 can be used for each gas to be investigated, the separating channel 4 of the respective analyzer having been configured specifically for the gas to be investigated.

Figure 8:
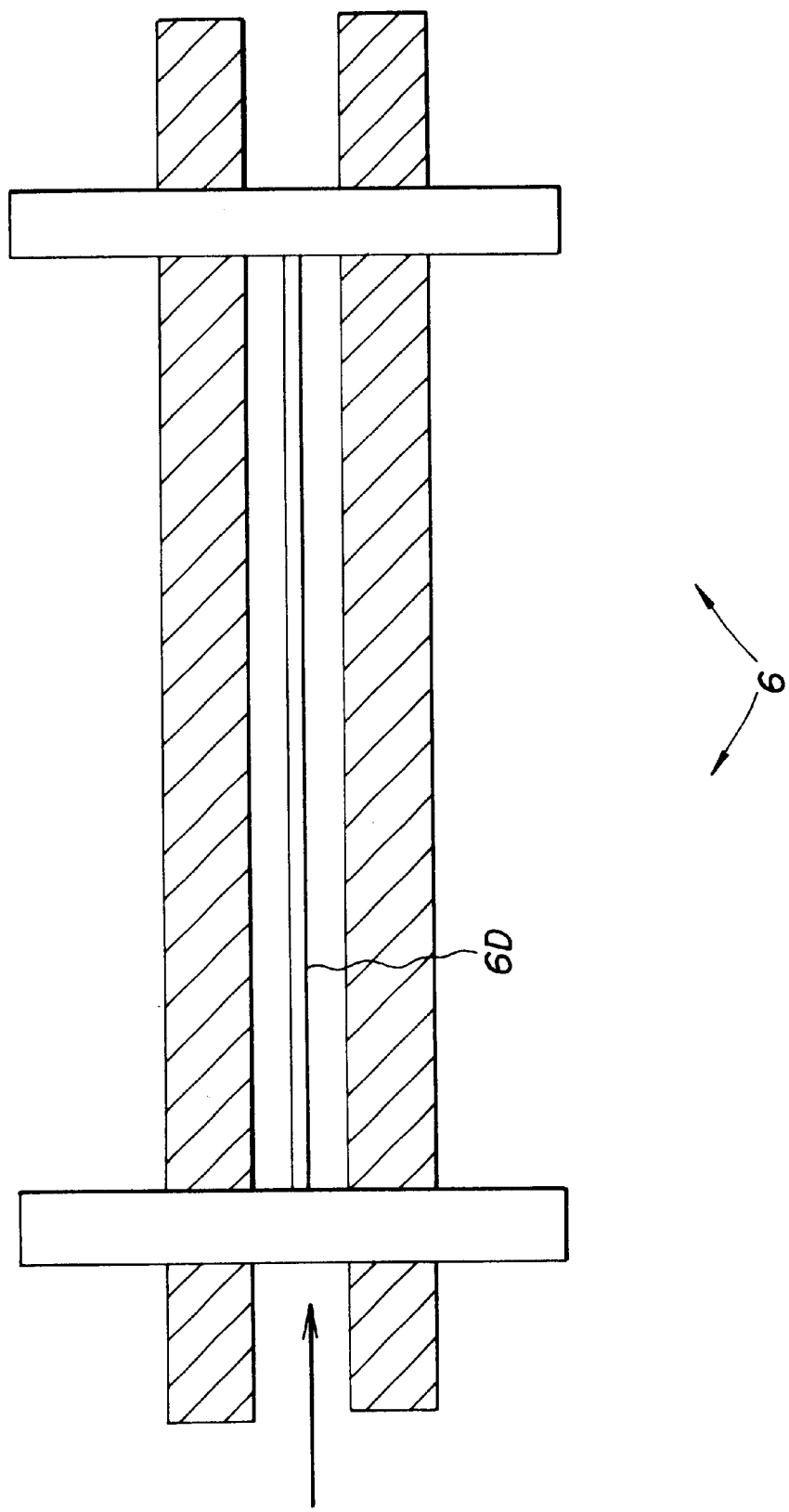
FIG. 8 is an illustration of a detector.

As FIG. 8 shows, the detector 6 is configured as a linear hollow body. Its first end is connected, as FIG. 2 shows, via the discharge line 16 to the output of the separating channel 4. Inside the detector 6, a wire 6D is disposed parallel to the longitudinal axis of the detector 6. The wire 6D is connected to a measuring device (not represented here), with which the electrical resistance of the wire 6D is measured. The components of a gas to be investigated which come from the separating channel 4 are passed through the detector 6. The electrical resistance of the wire 6D is changed by each component of the gas. The construction and mode of operation of the detector 6 have long been known. They are therefore not explained in any more detail here.

Figure 9:
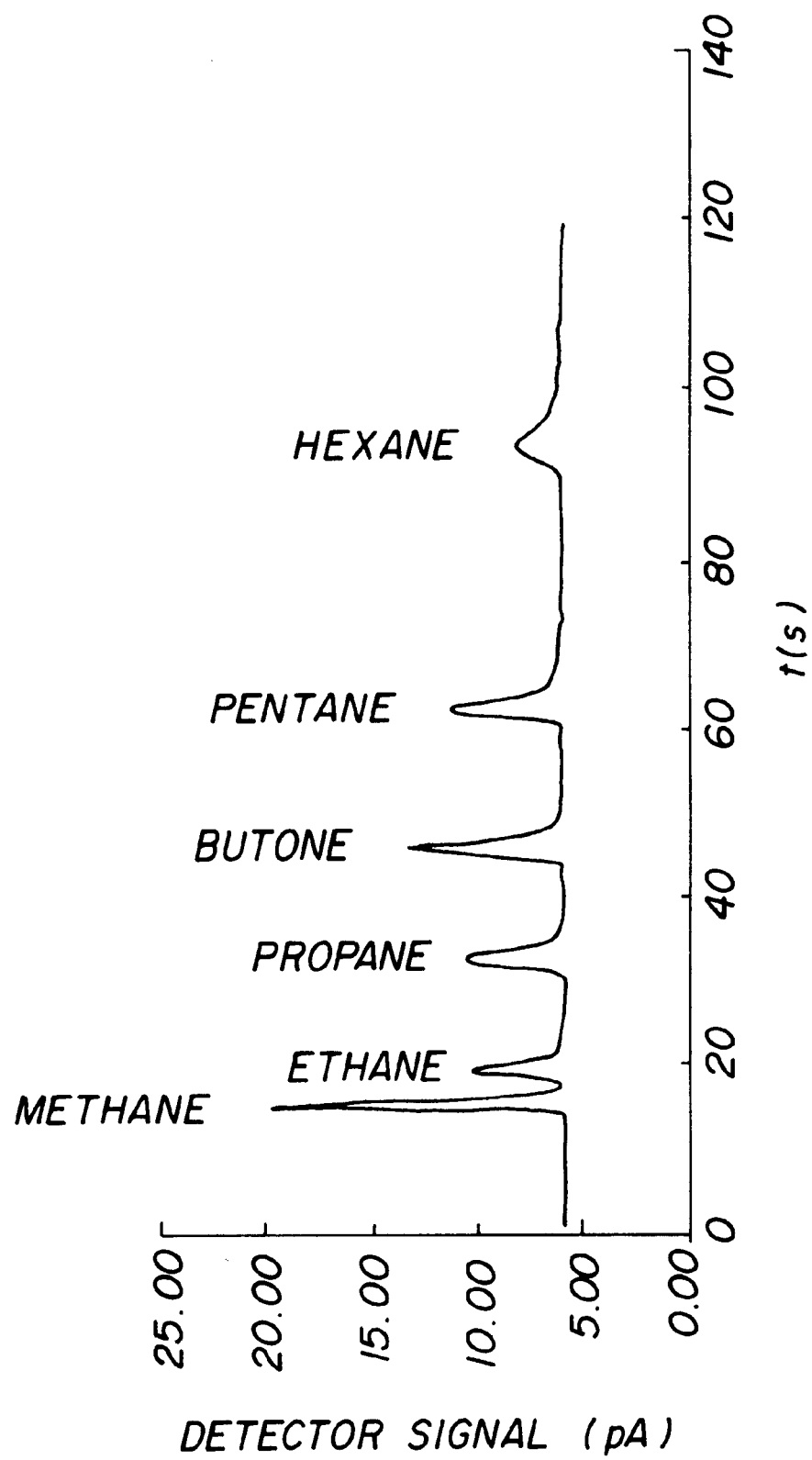
FIG. 9 is a graph showing a signal sequence at an output of the detector shown in FIG. 8.

A change in a voltage depends on how great a proportion of the total amount of the gas to be investigated is accounted for by this component. The time sequence with which the signals appear at the output of the detector 6 can be used to establish which components the gas to be investigated has, as represented in FIG. 9. Preferably, as represented in FIG. 10, a second detector 7 is connected upstream of the separating channel 4. This makes it possible to obtain measuring signals which are independent of the temperature, so that the accuracy of the measured values is improved. The output signals of each detector 6, 7 are fed via a signal line 34 to an evaluating unit 31 (FIG. 1), which is installed inside the central unit 3. The evaluating unit 31 is preferably a microprocessor. It is connected via a signal line to a display device 32, on which the measurement results can be read off. The display device 32 is likewise integrated into the central unit 3. The central unit 3 has, moreover, a power supply unit 37, which is provided for the electrical power supply of the entire measuring and evaluating device and can be connected to the gas analyzer 2 via a line 38, configured as a plug-in connection.

However, a flame ionization detector, a thermal conductivity detector or an electron capture detector may also be used as the detector 6, 7. The invention is not, however, restricted to the embodiments of detectors described here. Rather, all detectors suitable in terms of size and function can be used here.

Each gas analyzer 2 may, if required, also be equipped with more than one separating channel. In this case, a plurality of plates 10 are installed in the gas analyzer 2, at least one separating channel 4 being integrated into each plate 10 in the way represented in FIG. 5 and explained in the associated description. In this case, the sample injector 5 is connected via a non-illustrated distributor to the separating channel 4 or, if required, a plurality of the separating channels 4. The distributor is controlled by the evaluating unit 31. For this purpose, a signal line 35 according to FIG. 1 is provided, which line can be connected to the gas analyzer 2 via a plug-in connection (not represented here). A further distributor (not represented here), which is likewise controlled by the evaluating unit 31 via the signal line 35, is used for connecting the detector 6 to the output of the separating channel 4 being used at that time. Consequently, the investigation of different gases 42 is possible without the gas analyzer 2 having to be exchanged.

As FIGS. 2 and 3 show, the sample injector 5 of each gas analyzer 2 is provided with a respective supply line 21, 22 and 23 for the carrier gas 41, a gas 42 to be investigated and the calibrating gas 43. The supply lines 21', 22' and 23' may be connected via gastight plug-in connections (not represented here) to corresponding supply lines 21, 22 and 23 in the central unit 3. The gas to be investigated can be taken from a main line (not represented here), to which the supply line 21 of the central unit 3 can be connected. The carrier gas 41 may be taken, for example, from a storage tank (not represented here), to which the supply line 22 is connected. If hydrogen is used as the carrier gas 41, it may also be produced by electrolysis of water, which is located in a tank within the central unit 3 (not represented here). The calibrating gas 43 is preferably also taken from a storage tank (not represented here), to which the supply line 23 is connected. The detector 6 is provided with discharge lines 25', 26', 27' for the carrier gas 41, the gas to be investigated 42 and the calibrating gas 43. The discharge lines 25', 26', 27' may likewise be connected by plug-in connections (not represented here) to corresponding discharge lines 25, 26, 27 in the central unit 3. For the discharge of the gases coming from the detector 6 (not represented here) from the central unit 3 to the outside, a line 28 is provided. To be able to keep the gas to be investigated 42 at a certain temperature, or to be able to heat it up or else cool it to a defined temperature, a Peltier element 36, serving as a heating and cooling device 36, is installed in the central unit 3. The heating and cooling device 36 is in very close contact with the plate 10 of the gas analyzer 2, so that if need be very rapid heating or cooling can take place. According to the invention, the heating and cooling element 36 may also be disposed inside the gas analyzer 2 (not represented here). A resistance heater may also be used for heating and the Peltier element may also be used for cooling.

We claim:

1. A measuring and evaluating device for performing an analysis of a gas, comprising:

a central unit including an evaluating unit, a display unit, a power supply unit for electrical power, and supply lines for transporting a carrier gas, the gas to be analyzed and a calibrating gas;

a gas analyzer configured as a module to be connected directly to said central unit from outside, said gas analyzer automatically connected to said evaluating unit, said power supply unit for electrical power, and said supply lines for transporting the carrier gas, the gas to be analyzed and the calibrating gas upon being connected to said central unit;

at least one plate releasably fitted into said gas analyzer, said at least one plate having a separating channel, a sample injector to be connected from said evaluating unit to said separating channel and a detector to be connected to said separating channel, said sample injector having supply lines to be connected via a respective plug-in connection to each of said supply lines of said central unit; and a heating and cooling device provided in one of said gas analyzer and said central unit.

2. The device according to claim 1, wherein:

said plate has recesses formed therein functioning as said separating channel;

a covering closes off said separating channel; and a separating material is applied to inside surfaces of said recesses and to an inside surface of said covering facing said recesses, at least in a region of said separating channel.

3. The device according to claim 2, wherein said separating channel has a U-shaped cross section, and said plate and said covering are formed from a material selected from the group consisting of silicon, glass, metal and plastic, and said separating material is hexamethyl disiloxane.

4. The device according to claim 1, wherein said heating and cooling device is a Peltier element.

5. The device according to claim 1, wherein said heating and cooling device is formed of a resistance heater and a Peltier element.

* * * * *